United States Patent [19]

Cahill, Jr. et al.

[11] Patent Number: 4,594,434

[45] Date of Patent: Jun. 10, 1986

[54] PROCESS FOR THE DEPOLYMERIZATION OF POLYESTERS USING DAWSONITE AS THE CATALYST

[75] Inventors: Joseph Cahill, Jr., Ft. Mitchell, Ky.; Eugene G. Harris, West Chester, Ohio

[73] Assignee: National Distillers and Chemical Corporation, New York, N.Y.

[21] Appl. No.: 668,597

[22] Filed: Nov. 5, 1984

Related U.S. Application Data

[63] Continuation-in-part of Ser. No. 404,158, Aug. 2, 1982, abandoned.

[51] Int. Cl.[4] .................. C07D 323/00; C07D 313/00; C07D 327/00; C07D 327/02
[52] U.S. Cl. .................................... 549/267; 549/266; 549/10; 549/11
[58] Field of Search ..................... 549/267, 266, 10, 11

[56] References Cited

U.S. PATENT DOCUMENTS

| | | | |
|---|---|---|---|
| 2,092,031 | 9/1937 | Spanagel | 549/267 |
| 4,157,330 | 6/1979 | Rueter et al. | 549/267 |
| 4,165,321 | 8/1979 | Harris et al. | 549/267 |
| 4,221,771 | 9/1980 | Van der Heem | 423/419 P |
| 4,238,458 | 12/1980 | Misra | 423/115 |

FOREIGN PATENT DOCUMENTS

| | | | |
|---|---|---|---|
| 54-103884 | 8/1979 | Japan | 549/267 |
| 54-115390 | 9/1979 | Japan . | |
| 55-120581 | 9/1980 | Japan . | |

OTHER PUBLICATIONS

Chemical Abstracts, vol. 94 (1981) 102927r.
Dana's System of Mineralogy, vol. 2 (1951) pp. 276–278.

*Primary Examiner*—Norma S. Milestone
*Attorney, Agent, or Firm*—Kenneth D. Tremain; Gerald A. Baracka

[57] ABSTRACT

Dawsonite is a highly effective and useful catalyst for the thermal depolymerization of polyesters to produce macrocyclic compounds. High yields and enhanced rates of reaction are obtained using Dawsonite obtained from natural or synthetic sources.

5 Claims, No Drawings

PROCESS FOR THE DEPOLYMERIZATION OF POLYESTERS USING DAWSONITE AS THE CATALYST

CROSS REFERENCES TO RELATED APPLICATIONS

This is a continuation-in-part of our co-pending application Ser. No, 404,158, filed Aug. 2, 1982, now abandoned.

BACKGROUND OF THE INVENTION

Macrocyclic esters are obtained by the thermal depolymerization of the corresponding linear polyesters accompanied by ring closure. For such processes, the polyester is heated at an elevated temperature in the presence of a catalyst. The reaction is carried out under reduced pressure and the macrocyclic compound and other volatile products formed during the course of the depolymerization are removed from the reaction zone as they are formed.

Chlorides, nitrates, carbonates and oxides of magnesium, manganese, iron, cobalt and tin (all in the divalent state) are disclosed to be effective catalysts for the depolymerization of linear polyesters in U.S. Pat. No. 2,092,031. In the process of U.S. Pat. No. 4,165,321 Lewis metal salts such as the oxides hydroxides, halides, or carboxylates of Group IIIa, IVa, IVb, Va, VIIb and VIII metals are indictaed to be useful catalysts. Yasakawa et al. reported the use of lead catalysts (oxide, hydroxide, carbonate, nitrate, borate or organic acid salts) for the preparation of large ring lactones via thermal depolymerization in Chemical Abstracts, Vol. 78 (1973), 158966q and 158968s. Cyclic esters are also obtained via thermal degradation of polyesters using $SnCl_2 \cdot 2H_2O$ in Chemical Abstracts Vol. 86 (1977), 156163s. In U.S. Pat. Nos. 4,105,672, 4,136,098 and 4,157,330 tin carboxylates and organotin compounds are employed in conjunction with an 0,0-dialkyl-(3,5-di-t-butyl-4-hydroxybenzyl)phosphate to catalyze the reaction. In a somewhat related procedure, the formation of cyclic ester anhydrides of alpha-hydroxycarboxylic acids in vacuo by depolymerizing the corresponding linear polymer at 200°–240° C. in the presence of lead (II) stearate is described in British Patent No. 1,108,720.

In view of the problems associated with the use of heavy metal catalysts, aluminum oxide was suggested to catalyze depolymerizations carried out at atmospheric pressure using superheated steam in Czech Patent No. 108,762. The use of metallic aluminum was also reported in Japanese Patent No. 36-1375 (1961) for the thermal depolymerization of polyesters to form cyclic esters and lactones. Aluminum alcoholates are disclosed for the preparation of large-ring lactones in Japanese Patent Publication No. 72 25,071.

Mixed-metal catalysts having a carbonic acid radical and based on aluminum and sodium, wherein aluminum is the predominant metal, are disclosed for the depolymerization of polyesters to produce macrocyclic compounds in Japanese Patent Disclosure Nos. 1979-103,884 (appln. no. 1978-8,809); 1979-115,390 (appln. no. 1978-22,023); and 1980-120,581 (appln. no. 1979-26,741). The mixed-metal catalysts of these Japanese references all have aluminum:sodium weight ratios greater than about 3.5:1. The catalysts are typically prepared by treating an aqueous mixture of aluminum hydroxide and caustic soda with carbon dioxide.

It would be highly advantageous if other mixed-metal catalysts based on aluminum and sodium were available. It would be even more desirable if these new mixed-metal catalysts gave even faster reaction rates and if the catalysts were available from natural sources or could be synthetically produced.

SUMMARY OF THE INVENTION

We have now quite unexpectedly discovered that by utilizing natural or synthetic Dawsonite as the catalyst it is possible to significantly increase the rates of reaction for the production of macrocyclic compounds by the thermal depolymerization of polyesters.

For the present improved process a linear polyester is heated at a temperature in the range 200° C. to 400° C. under reduced pressure in the presence 0.01 to 10 weight percent Dawsonite, based on the polyester. Typically the depolymerization is carried out at a pressure from about 10 mm Hg to 0.01 mm Hg and the Dawsonite is present in an amount from about 0.1 to 5 weight percent, based on the polyester. Macrocyclic products having from 8 to 20 carbon atoms in the ring can be obtained by the process of this invention.

DETAILED DESCRIPTION

The present invention relates to a process for the depolymerization of linear polyesters accompanied by ring closure to form macrocyclic compounds having from 8 to 20 atoms in the ring. The process employs natural or synthetic Dawsonite as the catalyst for the reaction.

Polyesters used in these depolymerization processes are obtained by conventional methods known to the art. It is advantageous to use polyesters which are terminated with monocarboxylic acid(s) and/or monofunctional alcohol(s) to control the molecular weight and viscosity of the polymer. Polyesters having acid values and hydroxyl values less than about 20 and, more usually, less than 10 are particularly useful. The degree of polymerization of the polyesters will generally be between about 5 and 150 but can be higher, if desired. Useful polyesters are derived from conventional dicarboxylic acids, diols and hydroxymonocarboxylic acids. Dicarboxylic acids employed are preferably aliphatic and may be saturated or contain olefinic unsaturation and can be branched or straight-chain. Polyesters derived from aromatic or alicyclic dicarboxylic acids can also be employed, however.

The dicarboxylic acids will typically contain from 3 up to about 18 carbon atoms and, more preferably, from about 8 to 14 carbon atoms. Especially useful dicarboxylic acids include, for example, malonic acid, maleic acid, succinic acid, glutaric acid, adipic acid, pimelic acid, azelaic acid, sebacic acid, undecanedioic acid, dodecanedioic acid, brassylic acid, pentadecanedioic acid, and the like. Mixtures of two or more dicarboxylic acids may also be employed. Polyesters derived from $C_{9-13}$ saturated aliphatic dicarboxylic acids are especially preferred since macrocyclic compounds produced therefrom exhibit especially desirable fragrance properties and are useful in a wide variey of cosmetic applications.

Diols utilized for reaction with the aforementioned dicarboxylic acids are primarily aliphatic diols having from 2 to 12, and more preferably, 2 to 6 carbon atoms. The diols are preferably saturated and can be either straight-chain or branched. Useful diols include ethylene glycol, 1,2- or 1,3-propanediol, 1,2-, 1,3-, or 1,4- butanediol, 1,6-hexanediol, 3-methyl-1,5-pentanediol, 2,3-dimethyl-2,3-butanediol, 1,8-octanediol, 2-ethylhexanediol, 1,10-decanediol, 1,12-dodecanediol, diethylene glycol, triethylene glycol, and the like. Alicyclic diols such as 1,4-cyclohexadimethanol may also be employed. Polyesters derived from ethylene glycol and di-, tri- and tetraethylene glycol are especially advantageous for use in the depolymerization process.

Hydroxymonocarboxylic acids from which useful polyesters can be derived include 15-hydroxypentadecanoic acid, 16-hydroxyhexadecanoic acid, 10-oxa-16-hydroxyhexadecanoic acid, 11-oxa-16-hydroxyhexadecanoic acid, 12-oxa-16-hydroxyhexadecanoic acid, 10-thia-16-hydroxyhexadecanoic acid, 11-thia-16-hydroxyhexadecanoic acid, 12-thia-16-hydroxyhexadecanoic acid, and the like.

Employing polyesters of the above types, it is possible to obtain macrocyclic compounds having from 8-20 carbon atoms in the ring. The macrocyclic compounds will conform to the general formulae

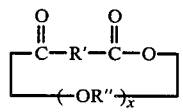 (a)

where R' is a bivalent aliphatic hydrocarbon radical, which can be branched or straight chain, saturated or contain unsaturation, having from 1 to 16 carbon atoms, R" is a saturated bivalent aliphatic hydrocarbon radical having 2 to 12 carbon atoms and x is an integer from 1 to 4;

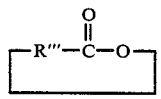 (b)

where R'" is a bivalent aliphatic hydrocarbon radical having from 6 to 18 carbon atoms: or

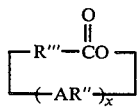 (c)

where R", R'" and x are the same as defined above and A is oxygen or sulfur.

Especially useful macrocyclic compounds of type (a) are those wherein the moiety R' is a saturated aliphatic radical having from 6 to 12 carbon atoms, the aliphatic radical R" has 2 to 6 carbon atoms, and x is 1 or 2. Preferred macrocyclic products of types (b) and (c) are those wherein R'" is a saturated bivalent aliphatic hydrocarbon radical having from 10 to 14 carbon atoms, the aliphatic radical R" contains from 2 to 6 carbon atoms, A is oxygen, and x is 1 or 2.

Illustrative macrocyclic products which can be produced by the depolymerization process of this invention include: 3,6,9-tridecamethylene malonate, dodecamethylene malonate, decamethylene malonate, ethylene suberate, ethylene azelate, 3-oxa-pentamethylene azelate, 3-methylpentamethylene sebacate, ethylene undecanedioate, ethylene dodecanedioate, ethylene brassylate, ethylene-alpha-methylbrassylate, ethylene-alpha-alpha-dimethylbrassylate, ethylene-alpha-ethylbrassylate, pentadecanolide, 12-oxa-pentadecanolide, 12-thiapentadecanolide, hexadecanolide, 10-oxa-hexadecanolide, 11-oxa-hexadecanolide, 11-thia-hexadecanolide, 12-oxa-hexadecanolide and the like.

The macrocyclic compounds obtained from the process are primarily useful in cosmetic applications. They impart desirable fragrance properties and/or enhance the fragrance characteristics of other compounds combined therewith. For example, they can be used in detergents (heavy duty and regular laundry), soaps (bar soaps, dish soaps and specialty beauty soaps), personal care products (bath oils, shampoos, hair rinses, deodorants, shaving creams and mouthwashes), and as fine fragrance components for perfumes, perfume oils, perfume fixatives, colognes, aftershave lotions and the like. Products obtained by the present process are particualrly adaptable to applications where heavy metal residues cannot be tolerated.

For the process of this invention, Dawsonite is utilized as the catalyst for the depolymerization-cyclization reaction. It has quite unexpectedly been discovered that substantially increased reaction rates, with high yields of the macrocyclic product, are obtained utilizing Dawsonite as compared to processes using the mixed-metal catalysts of the prior art.

Dawsonite is a basic carbonate of sodium and aluminum having a ratio of sodium:aluminum:carbon:oxygen:hydrogen of 1:1:1:5:2. It has been represented in the literature by the following formulae:
NaAl(CO$_3$)(OH)$_2$
Al$_2$O$_3$.Na$_2$O.2CO$_2$.2H$_2$O
AlNaO(OH)HCO$_3$
AlNa$_3$(CO$_3$)$_3$.2Al(OH)$_3$ Dawsonite is a naturally occurring mineral but it can also be produced synthetically, such as by the process described in U.S. Pat. No. 4,238,458. It is a colorless to white crystalline solid containing about 19% aluminum and 16% sodium, i.e., weight ratio of about 1.2:1 (Al:Na).

For this invention either the naturally occurring mineral or synthetic Dawsonite can be employed to produce the desired results. The amount of Dawsonite used will range from about 0.01 up to about 10% by weight, based on the polyester. Most generally from about 0.1 to about 5% by weight Dawsonite will be utilized for the process.

In addition to improving the reaction rate and providing high yields of the macrocyclic product, the process of this invention is also advantageous in that it avoids the use of heavy metals. The presence of even small amounts of heavy metals in macrocyclic products is detrimental. The presence of such metal contaminants promotes the formation of degradation products which impart undesirable color and/or odor to the macrocyclic product or otherwise detract from the overall desirable characteristics of the material.

The process can be carried out in accordance with established procedures. Thermal depolymerization reactions are well known and in this regard reference may be had to the prior art previously referred to. The depolymerization process is typically conducted at temperatures in the range 200° C. to 400° C. and, more usually, from 250° C. to 360° C. Subatmospheric pressures are employed to facilitate removal of the macrocyclic products formed. The process will generally be carried out at pressures less than about 50 mm Hg, and more preferably, the pressure will be in the range from about 0.1 mm Hg to 10 mm Hg.

The temperature, pressure and amount of catalyst employed for the process will vary depending on the particular polyester being depolymerized, the method of operation and design of the process equipment. The process can be carried out as a batch, continuous or semi-continuous operation employing conventional processing equipment adaptable to removal of the macrocyclic product formed during the course of the depolymerization reaction by vacuum distillation. The catalyst is equally effective in batch type operations or in continuous or semi-continuous operations such as described in U.S. Pat. No. 4,165,321. If the process is conducted in accordance with the latter procedure, the Dawsonite may be added continuously or incrementally throughout the course of the depolymerization.

That markedly superior rates of reaction are obtained utilizing Dawsonite (wt. ratio Al:Na of 1.2:1) as the catalyst for the process is truly surprising in view of the fact that the mixed-metal catalysts of the prior art have Al:Na weight ratios ranging from 3.5:1 up to 10.4:1. It is even more unexpected in view of the data presented in Japanese Patent Disclosure No. 1979-103,884 which indicates that as the weight ratio of Al:Na is decreased the depolymerization rate decreases.

The following examples illustrate the invention more fully but are not intended to limit the scope thereof. In the examples all parts and percentages are on a weight basis unless otherwise indicated.

EXAMPLE I

To prepare poly(ethylene brassylate) 109 parts dimethyl brassylate and 30.5 parts polymer grade ethylene glycol were charged to a resin kettle fitted with an agitator, distillation head and condenser. About 2.5% methyl esters of a mixture of $C_{16-22}$ fatty acids, based on the dimethyl brassylate, was included as a chain terminator. A supported titanium catalyst (0.08 parts), prepared from tetraisopropyl titanium and a naturally acidic montmorillonite clay in accordance with the procedure of U.S. Pat. No. 4,032,550, was then added under a positive pressure of nitrogen and heating commenced. When the temperature reached about 180° C. methanol began distilling from the reaction mixture and was collected. When most of the methanol was removed the temperature was increased to about 195°–205° C. and a vacuum applied. The vacuum was slowly increased to about 30 in. Hg and maintained for about 4 hours. The poly(ethylene brassylate) was then cooled to about 180° C. and filtered to remove the supported titanium catalyst. The resulting product had a viscosity of 117 cSt. at 210° C.

To a portion of the above-prepared poly(ethylene brassylate) was added 0.54 weight percent Dawsonite (obtained from Alcoa Chemicals, Bauxite, Ark.) and the poly(ethylene brassylate) depolymerized in accordance with the procedure described in U.S. Pat. No. 2,092,031. For the depolymerization a glass reaction vessel equipped with takeoff condenser was employed. The mixture was first heated at about 160°–180° C. and the Dawsonite thoroughly dispersed in the polymer. The temperature of the reaction mixture was then increased to 340° C. and maintained at a pressure of 1–1.5 mm Hg while removing the ethylene brassylate distillate. A 90% yield of crude ethylene brassylate was obtained after about 90 minutes and the poly(ethylene brassylate) was essentially completely depolymerized within two hours.

EXAMPLE II

In a manner similar to that described above, poly(ethylene brassylate) was depolymerized utilizing a synthetic Dawsonite prepared in accordance with the process of U.S. Pat. No. 4,238,458. For the catalyst preparation 43 parts sodium bicarbonate and 13.5 parts aluminum hydroxide were slurried in 264 parts water and the mixture heated for three hours in a stirred autoclave at 220° C. and 225 psig. The autoclave was then cooled to 50° C., vented and the reaction mixture filtered. The solid product was water-washed, air-dried, pulverized in a hammermill and sieved to less than 60 mesh. Analysis of the resulting synthetic product indicated 18.182% Al and 15.746% Na (theory: 18.8% Al, 16.0% Na). The synthetic Dawsonite was dispersed in poly(ethylene brassylate) at 0.59 weight percent level and the mixture heated to 340° C. (1–1.5 mm Hg). Ethylene brassylate was obtained in 87.7% yield in 90 minutes. When the synthetic Dawsonite was employed at a one percent catalyst level, a similar yield of ethylene brassylate was obtained and the poly(ethylene brassylate) was essentially totally depolymerized within 105 minutes.

EXAMPLE III

To demonstrate the markedly superior and unexpected results obtained with the process of this invention utilizing Dawsonite, the following comparative example utilizing a catalyst prepared in accordance with the teachings of Japanese Patent Disclosure No. 1979-115390 is provided. The catalyst was prepared following the procedure of reference example I of the Japanese application and contained 27.6% aluminum and 7.1% sodium upon analysis. The catalyst was dispersed in the poly(ethylene brassylate) at a 2.4 weight percent level and the depolymerization carried out in accordance with the procedure of Example I. Even though the catalyst loading was approximately four times greater (on a weight basis) than employed in Example I, after 90 minutes reaction time only 66% yield of ethylene brassylate was obtained. It is evident from the above data that the compounds of the Japanese reference are not as effective catalysts as Dawsonite for the depolymerization of poly(ethylene brassylate) even when employed at significantly higher levels.

EXAMPLE IV

Further evidence of the superiority of the present process which utilizes Dawsonite as the catalyst is evident from the following comparative experiments. For these two experiments, an amount of catalyst calculated to provide 0.76 weight percent aluminum, based on the weight of the poly(ethylene brassylate), was employed. For the first experiment (identified as IVA), the catalyst was a synthetic Dawsonite prepared in accordance with the procedure of Example II. In the second experiment (identified as IVB), a mixed-metal catalyst prepared in accordance with the procedure of Reference Example I of Japanese Patent Disclosure No. 1979-103,884 and containing 29.49% Al and 2.17% Na was utilized. Seventy grams poly(ethylene brassylate) was utilized for both experiments and the depolymerization was carried out at 340° C. and pressure of 1–2 TORR. The weight percent distillate recovered from the reactions was calculated at regular intervals in accordance with the equation:

$$\% \text{ Distillate} = \frac{\text{Weight Distillate}}{\text{Weight of Charge}} \times 100$$

The following results were obtained:

| Percent Distillate | Reaction Time (Minutes) | |
| --- | --- | --- |
| | IVA | IVB |
| 50% | 15 | 45 |
| 60% | 21 | 57 |
| 65% | 25 | 63 |

It is apparent from the above data that the reaction utilizing the Dawsonite catalyst proceeded about three times faster than the reaction which used the prior art catalyst.

When the reactions were repeated at a catalyst level calculated to provide 0.1 wt % Al, based on the polyester, the results were even more pronounced. Whereas 50% distillate was obtained from the Dawsonite catalyzed reaction within about 25 minutes, only about 11% distillate recovery was obtained in the same period of time with the prior art mixed-metal catalyst. Furthermore, even with prolonged heating (2 hours) it was not possible to obtain more than about 15% distillate recovery using the catalyst of the Japanese reference. With the Dawsonite catalyst, on the other hand, approximately 85% of the distillate is recovered within 45 minutes.

EXAMPLE V

To demonstrate the ability to carry out the process of this invention on a continuous basis, poly(ethylene brassylate) was depolymerized in accordance with the procedure of U.S. Pat. No. 4,165,321. For the reaction 0.54 weight percent Dawsonite was dispersed in the poly(ethylene brassylate) which was transferred to a stainless steel holding tank and maintained at 100° C. with agitation. From this tank the polyester was continuously metered into an electrically heated stainless steel inverted vertical cone reactor fitted with two conical helicoidal blades whose axes coincided with the cone axes of the bowl and which intermeshed as they were rotated in opposite directions to provide highly efficient top-to-bottom mixing throughout the total volume of the reaction mixture. The blades were positioned in the reactor so that the maximum blade-to-wall clearance was about 0.25° and driven with a high torque motor at about 20 rpm. For depolymerization the reaction mixture was maintained at a temperature in the range 330° C. to 360° C. and pressure from about 1 to 5 mm Hg. Ethylene brassylate was continuously distilled from the reactor and the rate of addition of the polyester containing the Dawsonite adjusted as necessary to maintain the proper material balance. The reaction was continuously operated for 32 hours with an overall yield of 79.5% crude ethylene brassylate being obtained.

We claim:

1. A process for the production of macrocyclic compounds having 8 to 20 carbon atoms in the ring and having the general formula

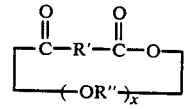

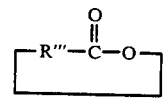

or

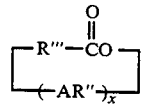

where R' is a bivalent aliphatic hydrocarbon radical having from 1 to 16 carbon atoms, R" is a saturated bivalent aliphatic hydrocarbon radical having from 2 to 12 carbon atoms, R'" is a bivalent aliphatic hydrocarbon radical having from 6 to 18 carbon atoms, x is an integer from 1 to 4, and A is oxygen or sulfur, which comprises heating the corresponding linear polyester at a temperature from 200° C. to 400° C. and pressure less than 50 mm Hg in the presence of 0.01 to 10% by weight, Dawsonite based on the polyester, to thermally depolymerize the polyester and removing the macrocyclic product formed.

2. The process of claim 1 wherein the Dawsonite is present in an amount from 0.1 to 5 weight percent, based on the weight of the polyester.

3. The process of claim 2 wherein the depolymerization is carried out at a temperature in the range 250° C. to 360° C. and pressure of 0.01 mm Hg to 10 mm Hg.

4. The process of claim 3 wherein the polyester is poly(ethylene brassylate) and the macrocyclic product is ethylene brassylate.

5. The process of claim 4 wherein the depolymerization is conducted as a continuous or semi-continuous operation.

* * * * *